(12) United States Patent
Boyd et al.

(10) Patent No.: US 9,893,261 B1
(45) Date of Patent: Feb. 13, 2018

(54) STRUCTURALLY EMBEDDED AND INHOSPITABLE ENVIRONMENT SYSTEMS AND DEVICES HAVING AUTONOMOUS ELECTRICAL POWER SOURCES

(71) Applicant: FACE INTERNATIONAL CORPORATION, Norfolk, VA (US)

(72) Inventors: Clark D Boyd, Portsmouth, VA (US); Bradbury R Face, Smithfield, VA (US); Jeffrey D Shepard, Norco, CA (US)

(73) Assignee: Face International Corporation, Norfolk, VA (US)

( * ) Notice: Subject to any disclaimer, the term of this patent is extended or adjusted under 35 U.S.C. 154(b) by 0 days.

(21) Appl. No.: 15/484,054

(22) Filed: Apr. 10, 2017

(51) Int. Cl.
| | |
|---|---|
| *H01L 21/00* | (2006.01) |
| *H01L 35/34* | (2006.01) |
| *H01L 35/02* | (2006.01) |
| *H01L 25/04* | (2014.01) |
| *H01L 25/00* | (2006.01) |

(52) U.S. Cl.
CPC .............. *H01L 35/34* (2013.01); *H01L 25/04* (2013.01); *H01L 25/50* (2013.01); *H01L 35/02* (2013.01)

(58) Field of Classification Search
CPC ......... H01L 25/04; H01L 25/50; H01L 35/02; H01L 35/16; H01L 35/34

USPC .......................................................... 438/54
See application file for complete search history.

(56) References Cited

U.S. PATENT DOCUMENTS

2011/0226299 A1* 9/2011 Makansi ................. H01J 45/00
                                                              136/203

* cited by examiner

*Primary Examiner* — Brook Kebede
(74) *Attorney, Agent, or Firm* — TannerIP PLLC; Daniel A. Tanner, III; James E. Gollady, II

(57) ABSTRACT

A method for producing an electrically-powered device and/or component that is embeddable in a solid structural component is provided. The electrically powered device includes an attached autonomous electrical power source in a form of a unique, environmentally-friendly structure that is configured to transform thermal energy at any temperature above absolute zero to an electric potential without any external stimulus including physical movement or deformation energy. The autonomous electrical power source component provides a mechanism for generating renewable energy as primary for the electrically-powered device and/or component once an integrated structure including the electrically-powered device is deployed in an environment that restricts future access to the electrical power source for servicing, recharge, replacement, replenishment or the like. The structure of the autonomous electrical power source component converts minimal thermal energy to a usable electrical power potential over a sustained period of time without external disturbance to the power source.

20 Claims, 8 Drawing Sheets

800

STRUCTURALLY EMBEDDED AND INHOSPITABLE ENVIRONMENT SYSTEMS AND DEVICES HAVING AUTONOMOUS ELECTRICAL POWER SOURCES

BACKGROUND

This application is related to U.S. patent application Ser. No. 15/095,061, entitled "Energy Harvesting Components And Devices", and Ser. No. 15/095,063, entitled "Methods For Fabrication, Manufacture And Production Of Energy Harvesting Components And Devices," each of which was filed on Apr. 9, 2016, and U.S. patent application Ser. No. 15/484,033, entitled "Autonomous Electrical Power Source," filed on Apr. 10, 2017, a same date as this application, and the disclosures of which are hereby incorporated by reference herein in their entirety.

1. Field of the Disclosed Embodiments

This disclosure relates to integrally-formed electrically-powered devices including unique, environmentally-friendly autonomous electrical power sources capable of being embedded in structures, and deployed in other environments, in which a sustainable, substantially permanent source of electrical energy is beneficial and in which accessibility to the electrically-powered devices, and the electrical power sources that drive those devices, may be restricted in a manner that may preclude servicing, recharge, replenishment or replacement.

2. Related Art

Recent technologic advances, particularly with the evolution of low-power solid state circuits and circuit components, have significantly increased the numbers and types of electronic systems, electronic devices, electronic system components, sensor systems/devices and wireless communicating components that require individual, scalable and often rechargeable sources of portable electrical power. Such systems and devices are routinely employed for communication, information exchange, manufacturing improvement, tracking/surveillance, health monitoring, personal entertainment and other like operational tasks. Machine-controlled processes improve information flow, manufacturing precision, information exchange, environmental control, system and area monitoring and individual convenience in virtually every area of daily life.

Electronic monitoring, sensor employment and communication finds advantageous employment in myriad real-world applications. Structures of all types are environmentally monitored and controlled by electronic sensor, anomaly detection, security and climate control components. Vehicles of all types include electronic navigation communication, and embedded electronic health monitoring systems. Electronic systems and devices in these structures and vehicles include a capacity to be locally monitored, as well as being remotely monitored at centralized locations, the remote monitoring providing extensive advantages to the owners and occupants of the structures and vehicles.

Electronic data exchange and communication have become an all-too-necessary staple of commercial efficiency and individual convenience. Cellular telephones, smartphones and other personal communication devices, often supported by powered wireless microphones, have become fairly ubiquitous in today's communicating environment. Wireless data exchange is a virtual necessity to many individuals as they undertake daily business and recreational tasks. Portable computing devices of all forms including tablet-type computers and other forms of hand-held personal digital assistant (PDA) devices, supported by an emerging class of wearable input/output (I/O) devices and interfaces, keep individuals' documents, personal and professional calendars, lists and contact information, reference and presentation materials, photo albums, music and other entertainment sources, and the like. These devices facilitate numerical calculations, timekeeping and all forms of data storage keeping close at hand necessary and/or desired information for a particular user in the conduct of his or her employment functions and personal tasks and/or enjoyment. Location and timekeeping data are constantly updated, and all types of pre-programmed data alerts and/or alarms are provided. Much of the locally-generated data input by users via their personal electronic devices is communicated to secure centralized locations as a "backup" to other means prevention of loss of that data, or otherwise for off-site analytics and the like.

At a comparable rate, miniaturized, transistorized, solid-state, and other powered devices and/or system components are finding their way increasingly into many and widely-varied technology areas. Robotic devices and other electronically actuated devices are increasingly replacing manual laborers in performing certain routine repetitive tasks, in implementing intricate computer-aided design and manufacturing of components and component structures that cross a broad spectrum of manufacturing and piece/part production functions, and in automating even the simplest environmental surveillance, monitoring and control functions. The precision available in the use of electronically machine-implemented instructions far surpasses that available by the efforts of even the most skilled artisan. Again here, the communication piece is important for records accumulation, remote analytics, system monitoring and control system update, among other beneficial functions.

Many technologies have been enabled and/or aided by the implementation of transistorized, miniaturized and other solid-state devices and device components. A broad spectrum of medical devices, for example, from digital thermometers to glucometers to hearing aids to pacemakers to all manner of personal health monitoring components, relying on miniaturized sensors and solid-state circuitry for monitoring, augmentation and communication of information regarding often-critical health parameters of individuals. Increasingly, individuals may be "fitted" or implanted with personal monitoring devices in order that they individually, or their physicians or others, may monitor all categories of health parameters.

Governmental, law enforcement and personal security and surveillance efforts and capabilities are implemented using fixed and mobile sensors. Many individuals and entities are making increasing use of arrays of fixed sensor components that are easily deployed and routinely monitored, as well as sensors field-deployed on a wide array of unmanned vehicles, including small unmanned aerial systems, carrying increasingly sophisticated monitoring and surveillance suites.

Particularized commercial embodiments of devices and systems that were not even conceived of a decade ago are finding their way into the commercial marketplace, many for making individuals' lives more convenient in the increasingly fast-paced world of data communication and information exchange. These include, for example, deployable and/ or monitorable security tokens by which individuals can track everything from their keys, to their luggage, to their kids, to their vehicles.

Enter what has been dubbed the "Internet of Things" or IoT, for short. The term IoT generally refers to an increasingly ubiquitous interactive networking of physical devices. Such devices may be any of those mentioned above installed in structures, buildings, open areas, machines, vehicles, and the like, or on any manner of electronic device, luggage, packaging and the like associated with, or conveyed by, any individual user. In current vernacular, many of these systems and/or devices are referred to as "connected" systems/devices or "smart" systems/devices to connote their connection to remote sources by which the systems and/or devices may be monitored, updated, controlled and the like. Individual system monitoring and communication components may be installed, embedded or otherwise included in electronic systems and sub-systems, software-operated devices, sensors, actuators and even the human body (or animal bodies) for the collection and exchange of data. As generally understood, the IoT provides a mechanism by which operating environments and operating parameters may be sensed or controlled remotely across differing networked information exchange infrastructures.

Advantages provided by the IoT may include advanced system monitoring and diagnostics for system and human failure detection and intervention, and broad-spectrum analytics. Other advantages may include advanced system and area monitoring for improved environmental control, physical and cyber security, and loss prevention. The IoT bridges the divide between sensor systems and physical devices in a manner that may reduce instances of required or desired human intervention to achieve particular results based on information collectible from connected sensors and actions implementable through connected actuators.

A variety of real-world scenarios are being explored from automated package tracking and delivery to control of "smart" power grids, virtual power plants and "smart" homes. The IoT may implement "intelligent" transportation systems, and even "driverless" vehicles. It is commonly understood that 50 billion objects will be connected to, monitored through, or controlled by aspects of, the IoT by 2020.

The scope of the "things" connected to the IoT is virtually boundless. Humans, animals, vehicles, packages, containerized shipments, currency, movable machinery and virtually anything else that is movable can be tracked with conditions, positions and environments being monitored and/or controlled. Buildings, structures, non-movable machinery, land masses, sea levels, waterways, ice floes, and atmospherics, generally anything that falls into a category of being considered substantially immovable, are also subject to monitoring and/or potential control. The overarching environment does not matter in that a location of a particular device on land, on or under the sea, in the air, or even in outer space may not restrict the ability to monitor and control activities via the "connected" device.

Network-connected devices may thus collect useful data with the help of various existing technologies and then generally share the collected data with other network-connected devices, centralized data collection, analysis, and control facilities, or data repositories. The data communication, collection, analysis and control capacity of the IoT, with billions of connected devices, necessitates movement and storage of a previously unforeseen mountain of data, which presents certain definable challenges.

A first challenge is with respect to the deconflicted communication of the data. For "incoming data," the need exists to deconflict billions of sensor signals to ensure that only those who should have access to particular elements of sensed data may be able to obtain such access. For "outgoing data," there is a coincident need to deconflict, for example, billions of generated control signals to ensure that the remotely generated signals control only those devices to which they are directed and intended to control, bypassing myriad connected, yet unintended, devices along a particular control signal transmission path.

A second challenge is with respect to storage and analysis of the mountain of data. The data needs to be stored in such a manner that it is sortable, to be made accessible to a particular user in real time. Otherwise, the collection of the data may be virtually useless. Data storage capacity will need to be increased dramatically over that currently available in both physical and virtual locations. Data sorting schemes will need to be streamlined to promote seamless rapid aggregation, indexing and processing of the data in order that it can be acted upon most efficiently, and in virtually real time.

A third challenge is with respect to security of the data in storage, and in transmission between multiple diverse locations across many and widely varied data transmission paths including wired, wireless and hybrid communication connections. One can easily foresee scenarios in which an ability to not only gain unauthorized access to data, but otherwise to generate incorrect, or improper, control signals may produce devastating consequences in the incorrectly, or improperly, controlled end devices or systems. The emergence and expansion of the IoT places renewed emphasis on countering MIJI (Meaconing, Intrusion, Jamming, and Interference), a problem with which militaries worldwide dealt decades ago, and over which some measure of success had previously been seen.

A fourth challenge, and perhaps that which poses the most significant "new" and unforeseen challenge because of its attenuation from the strict data exchange challenges outlined above, is with respect to that element that is common to all of electronic systems, electronic devices, electronic system components, sensors, controls, and the actuated or actuatable physical devices over which the IoT will afford individuals the opportunity to exercise control, is the requirement that all of the myriad system components be "powered."

Conventional power requirements take all forms. These include requirements to provide certain constant power supplies, for example, to volatile digital data storage components, security sensor components, health monitoring devices, timing units and the like. They also include separate and/or related requirements to be able to provide renewable or rechargeable on-demand power to any one of the above-mentioned communication, information exchange, sensor or actuator devices in a manner that allows those devices to be generally autonomously operated. For full implementation of the IoT, it is generally understood that there is a need to increase emphasis on "cutting the cord" in order that the largest percentage of the network connected devices can be operated apart from being tied to some bulky, or limited mobility, power source or power supply. The global power requirement to support the above non-exhaustive list of use cases, and to appropriately power the data sensing, data collection, data communication, control signal generation, control signal transmission, operational control implementation/actuation, and other tasks undertaken by the IoT with devices of every form, shape and function, is, in the aggregate, immense.

Supporting a global power requirement necessitates the expending of natural, naturally occurring, and/or manufactured/refined resources. The storehouse of available resources may have a limit at which those resources may be depleted. Concerns further arise not only regarding the ultimate availability of the resources, but also with respect to the adverse effects that may arise with respect to the conversion of certain of those resources to a usable energy production output.

Advancing research efforts and resultant technologies with regard to many of the above non-exhaustive list of use cases have, in many instances, systematically reduced the individual power requirements for providing intermittent, or even constant, power to myriad electronic devices, electronic components, sensors and actuators housed within larger component systems. Renewable energy technologies are pursued that seek to further reduce the global impact of overall energy production by attempting to meet increasingly-efficient power requirements or constraints, with increasingly environmentally-friendly energy sources. Despite the creativity in certain of the current research, it is generally understood that those research efforts in finding "smart" power sources are not keeping pace with the efforts at addressing the other challenges outlined above. Moreover, full implementation of the IoT may afford an opportunity to implement monitoring and control functions in environments which are generally inaccessible, incompatible with, or inhospitable to conventional electrical energy sources.

SUMMARY

As the individual electronic component or unit power requirements are reduced, it may be advantageous to find implementing electrical power generation and delivery strategies, and to design and fabricate autonomous electrical power generation components that could be usable in portable electronic devices, and the electronic components housed within such devices, for example, to supplant, or augment, chemical battery, or other source, power generation and delivery to those devices or components in an environmentally friendly, and renewably sustainable power source.

It may be further advantageous, where possible, to install autonomous electrical power generation components that are physically configured to provide a renewably sustainable source of generated electrical power on a semi-permanent basis without any necessity to be physically disturbed, deformed, moved or otherwise externally interacted with. In this manner, the autonomous electrical power generation components may be embedded in structures, or deployed in environments, in which routine servicing, replacement, recharge or replenishment of the power source may otherwise be considered impossible, or otherwise prohibitively expensive. The development of an appropriate autonomous electrical power source may enable specific classes of applications that are currently deemed desirable, but uneconomic.

Exemplary embodiments of the systems and methods according to this disclosure may provide an autonomous electrical power source that is uniquely configured to provide measurable electrical output for supplying power to electronic systems and electronic devices and/or electrically-powered system components, including communication, alert/warning, sensor and actuator elements.

Exemplary embodiments may provide an autonomous electrical power source that converts minimal amounts of thermal energy into a usable electrical power output at an atomic level and packages the accumulated usable electrical potential in a form that may be usable to power an electronic system, electronic device, and/or electrically-powered system component according to a generally renewable physical reaction for thermal conversion at the atomic level based on the component structure of the power source.

Exemplary embodiments may convert available thermal energy at virtually any temperature above absolute zero to a usable electrical potential in embodiments in which an ability to maintain a static electric potential between electrodes may be useful. The structure of the autonomous electrical power source may harness thermal energy from surrounding structures in a manner that produces a usable amount of electrical power according to a measurable and self-controlling physical reaction.

Exemplary embodiments may convert thermal energy at any temperature above absolute zero, and without physical movement or deformation of the power source or components thereof, to a usable electrical output from the disclosed autonomous electrical power source structure in order to continuously, or intermittently, power an electronic system, electronic device and/or electrically-powered system component, including, but not limited to, one or more of a communication, alert/warning, sensor, data exchange and actuating element.

Exemplary embodiments may provide a usable electrical power output at any temperature above absolute zero, and without exposure to any separate energy generating source, including kinetic disturbance, vibrational movement, physical deformation or the like being applied to the power source. In embodiments, the disclosed autonomous electrical power source may be usable to internally generate usable electrical power in environments that are devoid of any ambient light, and without any manner of external physical interaction with the structure of the autonomous electrical power source.

Exemplary embodiments may advantageously employ physical properties of particularly manufactured and conditioned conductors, at an atomic level, to beneficially employ characteristic electron motion, and channeling of that electron motion between conductors in a usable manner by optimally conditioning surfaces of opposing conductors to have measurably different work functions.

In embodiments, electrons are predictably and advantageously caused to migrate from a comparatively low work function surface of a first conductor in a direction of, and to accumulate on, a comparatively high work function surface of a second conductor thereby establishing an electric potential between the first and second conductors.

In embodiments, quantum tunneling effects are optimized to promote the electron migration from the low work function conductor surface and accumulation of the electrons on the comparatively high work function opposing (or facing) electrode surface.

Exemplary embodiments may optimize particular dielectric material structures interposed between the comparatively low work function conductor surface and the comparatively high work function facing conductor surface to promote optimized or enhanced rates of electron migration to, and accumulation on, the comparatively high work function surface of a facing electrode.

Exemplary embodiments may produce individual conductor-dielectric-conductor "sandwiched" electrical power generating elements.

Exemplary embodiments may aggregate pluralities of individual electrical power generating elements as particularly-formed autonomous electrical power source components for delivery of conditioned electrical power as a separate power source or as a supplement to another power source supplying power to electrical and/or electronic components.

Exemplary embodiments may provide particularly-formed autonomous electrical power source components for electrically powering integrated circuitry, and/or integrated circuits. In embodiments, the autonomous electrical power source components may be formed as a part, or portion, of the integrated circuit component.

Exemplary embodiments may provide autonomous electrical power source components that may be integrated with sensor and/or communication elements. In embodiments, integrated packages including the disclosed autonomous electrical power source components and one or more of sensor and communication elements may be permanently embedded in structures and/or structural elements at a point of manufacturer of those structures and/or structural elements to provide environmental and/or internal structural integrity sensing for the structures and/or structural elements throughout a useful or service life of the structures and/or structural elements in which communicating, sensor, actuating or other like devices powered by the autonomous electrical power source components may be embedded for use.

These and other features, and advantages, of the disclosed systems and methods are described in, or apparent from, the following detailed description of various exemplary embodiments.

BRIEF DESCRIPTION OF THE DRAWINGS

Various exemplary embodiments of the disclosed systems and methods relating to structures and implementations of a unique, environmentally-friendly autonomous electrical power source component for providing renewable energy, or a renewable energy supplement, in electronic systems, electronic devices and electrically-powered system components, will be described, in detail, with reference to the following drawings, in which.

DETAILED DESCRIPTION OF EMBODIMENTS

Figure 1:
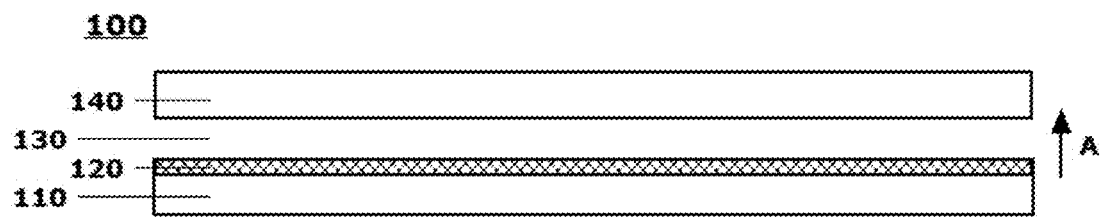
FIG. 1 illustrates a schematic diagram of a first exemplary embodiment of an autonomous electrical power source component constituent element according to this disclosure.

The systems and methods according to this disclosure relate to structures and implementations of a unique, environmentally-friendly autonomous electrical power source component having a thermal energy harvesting capacity for providing renewable energy, or a renewable energy supplement, in electronic systems, electronic devices and electrically-powered system components, including sensor, communication, alert/warning, and actuation elements. The disclosed autonomous electrical power source component may be particularly formed according to a micro fabrication process on the sub-micron scale to advantageously employ electron motion in a particularly advantageous manner to render a measurable electrical potential in, or to provide a measurable electrical output from, an autonomous electrical power source component composed of multiple "sandwiched" elements according to a particular combination of physical structures that combine certain physical effects to provide the output electrical power at virtually all temperatures above absolute zero, in ambient light devoid environments, and without physical disturbance or deformation of the structure of the autonomous power source components.

The disclosed schemes advantageously configure physical structures to channel electron motion, at the atomic or sub-atomic level, in a manner that provides a measurable and useful electrical output. Minimal amounts of thermal energy at any temperature above absolute zero may be collected and converted to usable output electrical power. As power requirements for certain electronic devices continue to decrease, the disclosed structures for micron sized autonomous electrical power source components may be advantageously employed to meet those power requirements, or to provide electrical energy conversion capacity by which to supplement other available power sources typically known to be provided for powering mobile and/or remote devices. The disclosed systems and methods may provide autonomous electrical power source components to be employed in environments in which routine servicing or recharge, or battery renewal, replenishment or replacement, currently presents a non-optimized operational configuration. In embodiments, the disclosed autonomous power source components may be embedded in structures in which, once embedded, access to the individual autonomous power source components, for any one or more of servicing, recharge, replacement and/or replenishment would be impossible. The disclosed autonomous power source component structures and capabilities, and the scalability of the resources and outputs, have been, in a first instance, experimentally reproduced in a laboratory environment.

Reference will be made to the employment of the disclosed exemplary autonomous electrical power source components to a number of real world beneficial purposes. The discussion of any particular use case for application of the disclosed schemes should not be considered as limiting the disclosed subject matter to employment with any particular class of electrical component, electrical circuit, electronic device, or any particular electrically-driven system component, including any communication, alert/warning, sensor or actuator element. It should be recognized that any advantageous use of the disclosed schemes for employing a particularly-configured autonomous electrical power source component according to the described embodiments to effect energy supply, or energy-supply supplementation, employing systems, methods, techniques, processes and/or schemes such as those discussed in detail herein is contemplated as being included within the scope of the disclosed exemplary systems and methods. In this regard, the disclosed systems and methods will be described as being particularly adaptable to providing measurable electrical power to certain electronic systems, electronic/electrical devices, and/or electrically-powered system components, including sensor, communication, alert/warning, actuator and other like elements, as easily-understandable and non-limiting examples of particularly advantageous uses of the disclosed autonomous electrical power source components. General reference throughout this disclosure will be made to particular use cases in which the disclosed autonomous electrical power source components may be usable in inhospitable environments, and embedded in structures, to convert minimal thermal energy to usable electrical power in scenarios in which routine servicing, replacement, recharge or replenishment may be difficult, if not impossible. Reference to any particular one of these use cases is not intended to exclude other use cases in which the disclosed structures for autonomous electrical power source components may be otherwise employed, including as micrometer-sized autonomous electrical power sources.

Reference to any particularly useful compositions of the materials from which the disclosed component layers of the autonomous electrical power source components may be formed and combined in the sub-micron scale are also descriptive only of broad classes of input materials that may be used. Suitable materials for such several Ångström-thick to tens of nanometers thick layers may be discussed specifically according to their composition, or may be more broadly referred to by certain functional parameters, neither of which should be considered to limit the scope of available input materials of which conductor layers, low work function layers and/or dielectric layers may be formed.

FIG. 1 illustrates a schematic diagram of a first exemplary embodiment of an autonomous electrical power source component constituent element 100 according to this disclosure. The disclosed schemes are directed to particular configurations of components for generating an electrical potential in the presence of minimal ambient heat or thermal energy. As shown in FIG. 1, a particular arrangement of the disclosed autonomous electrical power source component constituent element 100 may be in a form of a multi-layered component structure including at least a pair of opposing conductor layers (conductors) 110, 140 set at a particularly-measured small interval of less than 100 nm with respect to one another. The small interval between the conductors 110, 140 may be optimized to advantageously make use of a known quantum tunneling effect, as will be described in greater detail below. The spacing between the opposing conductor layers is critical in that arrangements with an interval spacing between the opposing conductor layers 110, 140 in a range in excess of approximately 200 nm may cause the electrical conduction phenomena according to this disclosure to cease.

Conductor 110 represents one of the output terminals for the accumulated electrical potential from the exemplary autonomous electrical power source component constituent element 100. A surface of conductor 110 facing conductor 140 may be conditioned in a manner described below to lower a work function of the facing surface of the conductor 110, e.g. to be in a range of less than 1.0 eV. In embodiments, this conditioning may be in the form of surface treating the conductor 110 with a particular low work function material, or in a form of depositing a separate particular low work function layer 120 on the facing surface of the conductor 110. This low work function layer 120 may be in intimate contact with the facing surface of the conductor 110 and may be relatively thin, on an order of Ångströms, e.g., not more than 20 Å, in thickness. The low work function layer 120 may have additional surface modifications made to it that further reduce a work function of the low work function layer 120.

A dielectric "layer" 130 may exist between the low work function layer 120 on the facing surface of the conductor 110, and the facing surface of the conductor 140. Those of skill in the art recognize that a dielectric layer may be in the form of a vacuum or an air gap, which is according to the depiction of the dielectric "layer" 130 in FIG. 1, and may also be in the form of a solid or liquid dielectric material, as shown in other exemplary embodiments discussed below. As noted above, the dielectric "layer" 130 is very thin, again on the order of Ångströms thick. Thus, a dielectric "layer" 130 in a form of an air gap, as depicted in FIG. 1, while possible, may be comparatively more difficult to engineer in that the dielectric "layer" 130 must maintain separation between the low work function layer 120 and the facing surface of the conductor 140 to avoid shorting between the opposing conductor 110, 140. As will be described in greater detail below with reference to the exemplary embodiment in FIG. 2, the dielectric layer may comprise a physical structure which may include piezoelectric particles incorporated on its outer surfaces, or throughout its structure.

Conductor 140 is the other of the output terminals for the accumulated electrical potential and is formed to have a facing surface with a relatively (or comparatively) higher work function (2.0 eV or greater) and a low resistance to reduce transmission losses. According to the mechanics of the disclosed schemes, the structure shown in FIG. 1, and in like manner the structures in FIGS. 2-4, may produce a static electric field that may be usable even without discharging elements, or attachment to a load, to produce, for example, a usable static electric field for employment in known use cases including for biasing a transistor. Importantly, the structure of the autonomous electrical power source component constituent element 100 provides for the accumulation of an electrical potential in instances in which the autonomous electrical power source component constituent element 100 is not subjected to any physical movement, physical deformation of any of its constituent elements, or any physical disturbance whatsoever.

It is known that electrons have a certain amount of energy that is generally described according to Schrödinger's wave equation. Work function is the energy required, usually specified in electron volts (eV), for the electrons to leave a surface of a material (often a metal surface) and to migrate, for example, into a vacuum facing the surface of the material. In solid-state physics, the work function is the minimum thermodynamic work (i.e., energy) needed to remove an electron from a surface of a solid to a final electron position separated from the surface of the solid on the atomic scale, but still close enough to the surface of the solid to be influenced by ambient electric fields. The work function is not a characteristic of the bulk material, but rather is a property of the surface of the solid or material.

As temperature increases above absolute zero, the electrons become more energetic and more easily leave the surface of the solid. When below the energy required by the work function for the electrons to leave the surface of the solid, there is only a small probability that the electrons will leave the surface. In other words, this is not a purely on and off function. Statistically, a particular electron may have more energy than the average energy of the surrounding electrons and may more easily migrate away from the surface of the solid. Random electrons may still leave the surface even when the temperature is below that which the work function indicates may allow the electrons to be energized enough to more freely leave the surface. As a work function of a particular surface is decreased in a donor (or emitter) surface, as in the surface conditioning of conductor 110 with a low work function layer 120 described above, or according to any one of a number of different mechanisms (as will be described below), it becomes easier for larger numbers of electrons to leave the donor or emitter surface and migrate toward the receptor surface with the comparatively higher work function. It is more difficult for electrons to freely leave the receptor surface based on the higher work function.

A simplified description of the operation of the structural embodiments according to this disclosure may be characterized as follows. The work function of the free electrons in the conductor 110 is lowered enough by surface conditioning, or the presence of the low work function layer 120, such that the free electrons leak into and through the very thin, i.e., Ångströms thick, dielectric "layer" 130 in direction A by the mechanism of quantum tunneling at room temperatures. A similar process is occurring in the opposite direction from conductor 140, but at a rate that is orders of magnitude lower due to the relatively or comparatively high work function of the material of the facing surface of conductor 140.

When a particularly low work function (less than 1.0 eV) material, e.g., silver oxide cesium, is employed as the donor or emitter surface, a comparatively larger number of electrons leave the surface at room temperature. When another surface is employed, like copper or gold, which has a comparatively higher work function (more than 2.0 eV and in a range of 5.0 eV or more) at room temperature then the donor or emitter surface releases comparatively much larger numbers of electrons than the receptor surface. It should be noted that differences in work function in the opposing conductor faces or surfaces of as little as 1.0 eV may produce usable electrical output from the disclosed structures for the exemplary autonomous electrical power source component constituent element 100. Quantum tunneling effects are a necessary component of the disclosed schemes and are implemented through the minimal proximities (less than 200 nm), across the dielectric layer 130, of the facing surfaces of the conductors 110, 140 and the presence of the low work function conditioning, or low work function layer 120, on the surface of the conductor 110.

At rest, given the proper combination materials, there is always going to be energy transfer from the donor or emitter surface to the receptor surface based on the above-described designed differences in work function of the respective surfaces. In this manner, the transfer of electrons, in a managed and predictable manner, is directed from a particular donor or emitter surface to a particular receptor surface. In embodiments, this is accomplished by conditioning the respective surfaces and placing them in properly close proximity to each other. The unique design placement of the respective layers generally described above results in a previously unforeseen, and previously unachievable, measurable electrical power potential accumulation on the receptor surface.

The electron migration process described above continues until the electric potential is high enough to stop further accumulation of electrons in the facing surface of the receptor, conductor 140. The electron accumulation on the facing surface of conductor 140 may be substantially equivalent to the electron depletion in the conditioned facing surface of conductor 110.

When an electrical circuit is completed between the conductors 110, 140 (in a manner similar to that shown in FIG. 5) electrons flow via the electrical circuit pathway from the conductor on which the electrons are accumulated (the receptor conductor with the comparatively high work function facing surface) to the conductor from which the electrons migrated across the dielectric layer internal to the autonomous electrical power source component constituent element 100 (the donor or emitter conductor with the comparatively low, and/or conditioned, work function surface) to equalize the charges. Thus, the collected thermal energy manifested as controlled electron migration between respective conductor surfaces is converted to electrical energy. With the static equilibrium state having been disturbed, the migration of electrons from the donor or emitter surface to the receptor surface re-commences.

The donor or emitter surface conductor 110 and the receptor surface conductor 140 may be comprised of high quality conductor materials in order to complete the electrical path by conducting electricity well, i.e., with little inherent resistance. To drive a lower work function in a surface of the conductor 110, a different material may be combined with the conductor 110 by, for example, surface treating the conductor 110 with an oxide and potentially nitrogen to turn the surface of the conductor 110 into a form of a semiconductor lowering the work function of the surface of the conductor 110. As indicated above, it is not a matter of what happens throughout the mass of the conductor 110, but rather what happens with electron migration at the surface. The material from which the conductor 110 is formed, therefore, is chosen to provide a good conduction to complete the electrical path.

Figure 2:
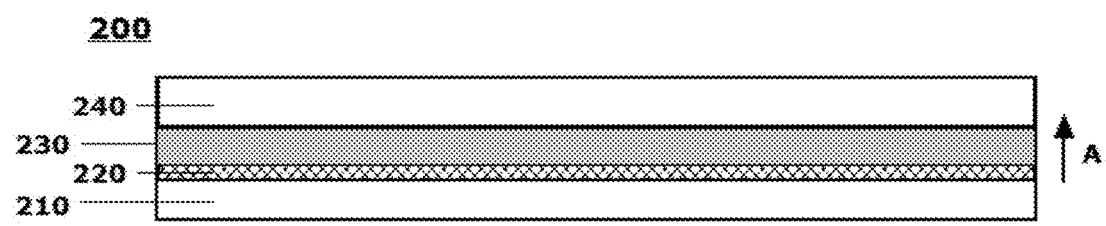
FIG. 2 illustrates a schematic diagram of a second exemplary embodiment of an autonomous electrical power source component constituent element according to this disclosure.

FIG. 2 illustrates a schematic diagram of a second exemplary embodiment of autonomous electrical power source component constituent element 200 according to this disclosure. As shown in FIG. 2, a particular arrangement of the disclosed autonomous electrical power source component constituent element 200 may again be in a form of a multi-layered component structure including at least a pair of opposing conductor layers (conductors) 210, 240 set on either face of a thin (less than 100 nm, and in embodiments on an order of 20-60 nm) dielectric layer 230. Again here, it must be noted that this particular sizing of the dielectric layer 230 is critical in achieving the accumulation of the electrical potential in the autonomous electrical power source component constituent element 200 in the absence of any external physical disturbance or deformation of the structure of the autonomous electrical power source component constituent element 200.

Typical conductor materials, by themselves, exhibit comparatively high work functions without a semiconductor or other surface treatment. As a result, any opposing conductor 240 may, in an unconditioned state, have a surface that inherently displays a comparatively high (or higher) work function. Because a dielectric layer in a form of a vacuum or an air gap in the manner shown in FIG. 1 may present certain challenges in a repeatable manufacturing process based on the small clearances between the low work function layer and the high work function facing surface of the opposing conductor, presence of a dielectric composition (solid or liquid) may provide a formed dielectric layer 230 in order to ensure positive, consistent and/or controllable separation between the low work function surface of conductor 210, or the low work function layer 220, and the facing surface of the opposing conductor 240 to avoid shorting therebetween.

The presence of the material structure of the dielectric layer 230 addresses a difficulty in how to maintain opposing conductive layers nanometers apart over comparatively large areas based on the proportional scales at which the autonomous electrical power source component constituent elements 200 may be manufactured. The dielectric (or semiconductor) layer 230 may substantially ensure that the electrons transfer from the low work energy surface 220 to the comparatively higher work energy surface of the conductor 240, while also ensuring that the two conductors 210, 240 do not internally short to one another, particularly based on an imperfection in a surface topography based on the critical tolerances and the infinitesimally small clearances between the opposing surfaces. The presence of the formed dielectric layer 230, or a presence of any dielectric, does not determine a direction of the flow of electrons (see arrow A). That direction of flow is determined according to the differential work functions in the respective donor or emitter, and receptor, surfaces. The dielectric layer 230 does, however, provide the spacer for facilitating the flow of electrons from the low work function surface layer 220 to the high work function facing surface of the opposing conductor 240. This positive separation ensures that the only path by which electrons can return to the low work function surface is through any attached load. See FIG. 5.

It has been long recognized that a very weak, but manageable, transfer of electrons is exhibited, or may be facilitated, between surfaces at a particular temperature, i.e., with no temperature differential between the surfaces, conceptually in contravention of the Second Law of Thermodynamics. See generally Fu et al., "Realization of Maxwell's Hypothesis—A heat-electric conversion in contradiction to Kelvin's statement," arXiv:physics/0311104 [physics.gen-ph] (Nov. 20, 2003) (describing an electron transfer phenomenon in an induced magnetic field where both parallel surfaces are at a same temperature, theoretically violating the Second Law of Thermodynamics). The disclosed schemes for particularly presenting structures in which opposing surfaces of conductor layers are conditioned to have differentiable work functions, and are placed in close enough proximity to substantially ensure a quantum tunneling effect overcome the shortfalls, which those of skill in the art generally accepted, in providing consequential and usable electrical power out of the disclosed autonomous electrical power source component constituent elements.

As mentioned above, quantum tunneling is an essential characteristic of the disclosed embodiments. The tunneling effect can be effectively controlled. At about a 200 nm or greater gap, the tunneling effect essentially disappears. At around 20 nm, however, the exponential function of the current increases significantly. A wave function begins to overlap the receptor conductor as the gap between the conductors is precisely controlled in a range of 100 nanometers or less, increasing in a range of 50 nm or less and increasing further in a range of approximately 20 nm. Based on this overlap, the free electrons can be trapped by the high work function surface to become a part of the free electron cloud of the receptor conductor. The high work function surface maintains its high barrier against release, significantly restricting residual release of electrons, potentially for tunneling, back in the other direction.

Not only are the compositions of the surfaces important according to materials from which they are formed, the internal topography of the donor (or emitter) and receptor surfaces are also important (the texture is important on a molecular level). In areas in which a surface topography comes to a sharp point, clusters of atoms are collected and/or congregated. At these points, the electric field is particularly focused. Any allegedly completely flat surface will include certain texture in its surface topography, in the sub-micron or Ångström scale, that will promote higher tunneling effect in the respective raised areas. Embodiments that take additional advantage of this phenomenon may be described below with respect to, for example, FIGS. 3 and 4 by particularly advantageously employing structural modifications to enhance these tunneling effects.

A unique enhancement in the disclosed layered arrangement schemes lies in consistently structurally implementing these quantum tunneling effects that are not seen at a macro-level. It is the channeling of this quantum tunneling effect, occurring with gaps between the conductors in a range of 200 nm or less, that causes (or promotes) enough electron transfer to generate an effective and measurable current through the load, and particularly where the conductor layers are separated in the tens of nanometers range from one another.

The dielectric layer 230 may be formed of candidates including aluminum oxide (AlO3) and Paralyne. Dielectric candidates with large bulk gaps include fluorinated Stanene. The dielectric layer 230 may be very thin, in a range of a monolayer of atoms or molecules to layers that are upwards to, but not greater than, 2000 times that thickness, i.e., up to 200 nm or so. The dielectric layer 230 may be uniform or varied in material composition. It also may be fully densified or porous with gas or vacuum within any voids that may be present. The dielectric layer 230 is intended to minimize electrical conduction. In embodiments, the dielectric layer may be 20 to 60 nm, to as much as 100 nm, thick in order to increase the quantum tunneling effect. A thinner dielectric layer 230 may be preferable in its capacity to promote higher electron migration according to the quantum tunneling affects, better utilizing a tail of the wave function. The thicker the dielectric layer 230 beyond 100 nm, for example, significantly reduces the quantum tunneling effect, until such effect ceases to occur in thicknesses of the dielectric layer 230 in excess of 200 nm. The lower limit to a thickness of the dielectric layer 230 may be restricted based on the composition of the material from which the dielectric layer 230 may be formed in that, at very thin layers in a range of, for example, 10 nm or less, dielectric breakdown may occur under certain circumstances.

The effects that may be harnessed according to the disclosed schemes are based on the presence of the low work function surface. The high work function surface will generally be at a work function in a range of 2+eV compared to 1.0 eV or less, for example, 0.8-0.6 eV (and theoretically even as low as 0.1 eV) in the low work function surface. When these surfaces are brought into the near contact with one another, separated by a dielectric layer in the manner described above, electron transfer occurs at a previously unanticipated rate. This electron transfer causes an electrical potential to accumulate in the layered structure of the autonomous electrical power source component constituent elements of the structures shown in FIGS. 1 and 2, described above, and FIGS. 3 and 4, as will be described in further detail below. As with any other electrical power source, when a load is connected to the disclosed autonomous electrical power source, certain depletion of the electrical potential occurs. Consider that the electrons flow from the high work function surface conductor through the load to the low work function surface conductor. The equilibrium between the low work function surface and the high work function surface is disturbed and electron transfer between those surfaces re-commences or continues in a sustainable manner as the electron transfer through the load may be controlled.

In a particular embodiment, the low work function layer may be comprised of a carbon nitride film deposited by, for example, an RF reactive magnetron sputtered graphite carbon in an N2 discharge. The effective work function for the carbon nitride films may be determined using the Fowler-Nordheim equation to be in a range of 0.01-0.1 eV. The substrate temperature of 200° C., floating potential at the substrate, and nitrogen partial pressure of 0.3 Pa may be favorable to promote the reaction that lowers the work function. Emitting-current density (J) may follow the Fowler-Nordheim (FN) relation:

$$J = \frac{AE^2}{\varphi} \exp\left(-\frac{B\varphi^{3/2}}{E}\right)$$

where A and B are constant, is the dimensionless field enhancement factor, and E and φ are the external electric field and the work function, respectively. From this relationship, reducing the work function is mathematically shown as an effective means to enhance electron transfer/migration according to this equation. Apart from, or in addition to, selecting particular materials for reducing the work function of, or associated with, a first conductor, possible physical mechanisms of reducing the work function may include the charge tunneling, surface roughening, or nano-structuring that enlarge the local curvature of the surface of the donor or emitter conductor. Chemical adsorption may be employed as well, noting, however, that only the field emission governed by the chemical adsorption on the surface of the conductor is intrinsic.

A non-limiting list of candidate substrates and/or surface treatments, in addition to those mentioned above, includes the following:
  Single layer graphene
  Lanthanum hexaboride or LaB6
  Double-Barrier Quantum Well Structure (AlSb/GaSb/AlSb resonant tunneling diode structure)
  Carbon nitride coating
  Carbon nitride plus boron nitride surface film
  AgOCe
  Ga-doped ZnO nanoneedle surface for enhanced electric field gradient
  Conductor surface treating with an ionization process
  RF-reactive sputtered graphite carbon The differential in work function between the higher work function layer and the low work function layer may be mediated, controlled or otherwise adjusted (even optimized) based on a composition of the material forming the intermediate layers at or between the surfaces of the donor and receptor layers of the conductors, or, for example, based on differential surface treatments of the individual donor and receptor surfaces of the conductors. For the purposes of this disclosure, a surface treatment of the donor or receptor surfaces of the conductors may be, or otherwise contribute to, the intermediate layer structure, including the dielectric layer, separating the donor and receptor surfaces.

Exemplary embodiments described and depicted in this disclosure should not be interpreted as being specifically limited to any particular configuration of an autonomous electrical power source component constituent element structure, except insofar as particular dimensions, as disclosed, are determined to be critical to enhancing the described electrical power generation capabilities. Additionally, although candidate materials may be specified for each of the conductors, the low work function surface layer or surface layer conditioning, the dielectric layer and the like, the disclosed embodiments should not be interpreted as being limited to any of the specific examples cited, or to any particular individual materials for forming the particular layers of each of the exemplary autonomous electrical power source component constituent elements.

Figure 3:
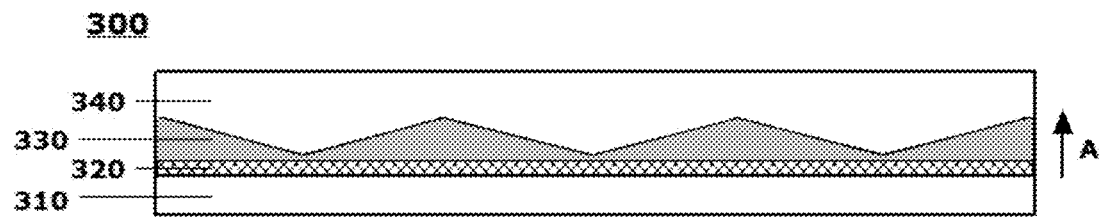
FIG. 3 illustrates a schematic diagram of a third exemplary embodiment of an autonomous electrical power source component constituent element according to this disclosure.

FIG. 3 illustrates a schematic diagram of a third exemplary embodiment of an autonomous electrical power source component constituent element 300 according to this disclosure. As shown in FIG. 3, a particular structure of the disclosed autonomous electrical power source component constituent element 300 may again be in a form of a multi-layered component structure including at least a pair of opposing conductor layers (conductors) 310, 340 set on either face of a thin (typically less than 100 nm, and in embodiments on an order of 20-60 nm) dielectric layer 330.

FIG. 3 depicts certain variation in a structure of the dielectric layer 330. The dielectric layer 330 may, in the same manner described above with regard to the dielectric layer 230 depicted in FIG. 2, be porous on a nanoscale, and generally less than 200 nm in overall thickness. A particular compound may be placed in the pores. Those of skill in the art recognize that not all materials are, in fact, porous on the nanoscale. There are certain materials that are "densified" enough to be nonporous, even on the nanoscale. In these materials, there is not an opening large enough for even the smallest atom to fit through. When certain material formation techniques are undertaken including, for example, vapor deposition, a particular material may be rendered nonporous on the atomic or nanoscale. In embodiments, the dielectric layer 330 may be porous in order that the other material can be inserted in the pores.

In embodiments, the other material may be comprised of metal cations in a water solution, for example, that can enhance the thermal energy harvesting capacity of the overall structure. Examples of the metal cations include: Nickel Chloride, Copper Chloride, Ferric Chloride, Potassium Chloride, or most metal Sulfates, Iodides, Bromides, and/or Fluorides.

Further, FIG. 3 is intended to depict a side view of the dielectric layer 330 formed to have a nonlinear pattern. Such a feature in the physical construct of the dielectric layer 330 may enhance the activity (motion) of the electrons through the dielectric layer 330 between the low work function surface 320 of the conductor 310 and the high work function surface of the conductor 340. The nonlinear structure, or patterning, in the dielectric layer 330 enhances the thermal activity of the electrons. A non-linear structure to the dielectric layer 330, as included in this disclosure, refers to a locally or overall tapered microstructure which will induce significantly enhanced activity (motion) of the electrons at the "small" ends or locally small end portions, as will be further described below.

Figure 4:
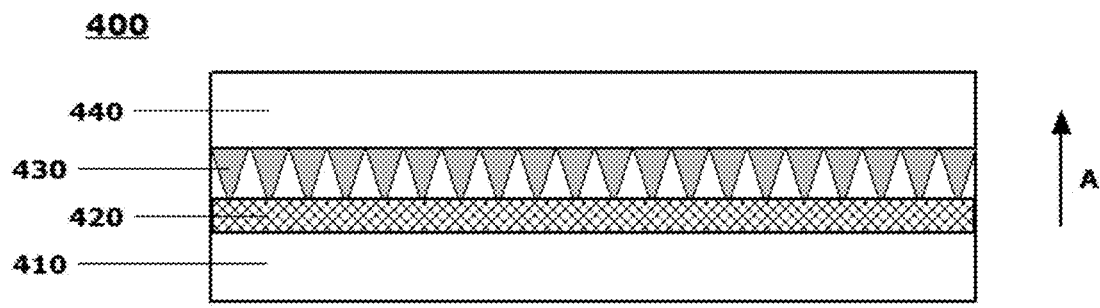
FIG. 4 illustrates a schematic diagram of a fourth exemplary embodiment of an autonomous electrical power source component constituent element according to this disclosure.

FIG. 4 illustrates a schematic diagram of a fourth exemplary embodiment of an autonomous electrical power source component constituent element 400 according to this disclosure. As shown in FIG. 4, a particular arrangement of the disclosed autonomous electrical power source component constituent element 400 may again be in a form of a multi-layered component structure including at least a pair of opposing conductor layers (conductors) 410, 440 set on either face of a thin (typically less than 100 nm, and in embodiments on an order of 20-60 nm) dielectric layer 430. A low work function surface treatment, or low work function surface layer 420 may be applied to a face of the conductor 410 to promote electron migration from the surface of the conductor 410, or from the surface layer 420, in a direction of a surface face of an opposing conductor 440 in direction A as shown.

FIG. 4 depicts another variation in a structure of the dielectric layer 430. In this embodiment, the dielectric layer 430 may be particularly formed, at least in part, as a series of horn structures the small end of the horns terminating at the low work function layer 420. Such a structure may enhance the activity of the electrons at the interface of the low work function layer 420 with the small ends of the horned structure of the dielectric layer 430 making it easier for the electrons to escape the low work function layer 420. Ionic liquids may be employed to fill the voids in the dielectric layer 430 created by such a structural arrangement. For embodiments intended to be used in particularly cold environs, the liquid dielectric component may be excluded. As depicted, broad ends of the horn structures of the dielectric layer 430 may contact the high work function surface of the conductor 440.

Regarding these conical shapes, because the energy is equal to one half the velocity squared times the mass ($E=1/2\ mv^2$), as a cross-section decreases and the mass therefore decreases, in a resonant structure, the velocity must increase a square root of the decrease in the mass. The taper may be adjusted based on the acoustic impedance and velocity of the material so that the energy distribution remains uniform, thus translation toward the smaller end requires increasing velocity. The electron energy, therefore, is further enhanced simply by a unique configuration of the mechanical structure of the dielectric layer 430, still with an overall thickness in a range of 200 nm or less, and preferably 100 nm or less.

Figure 5:
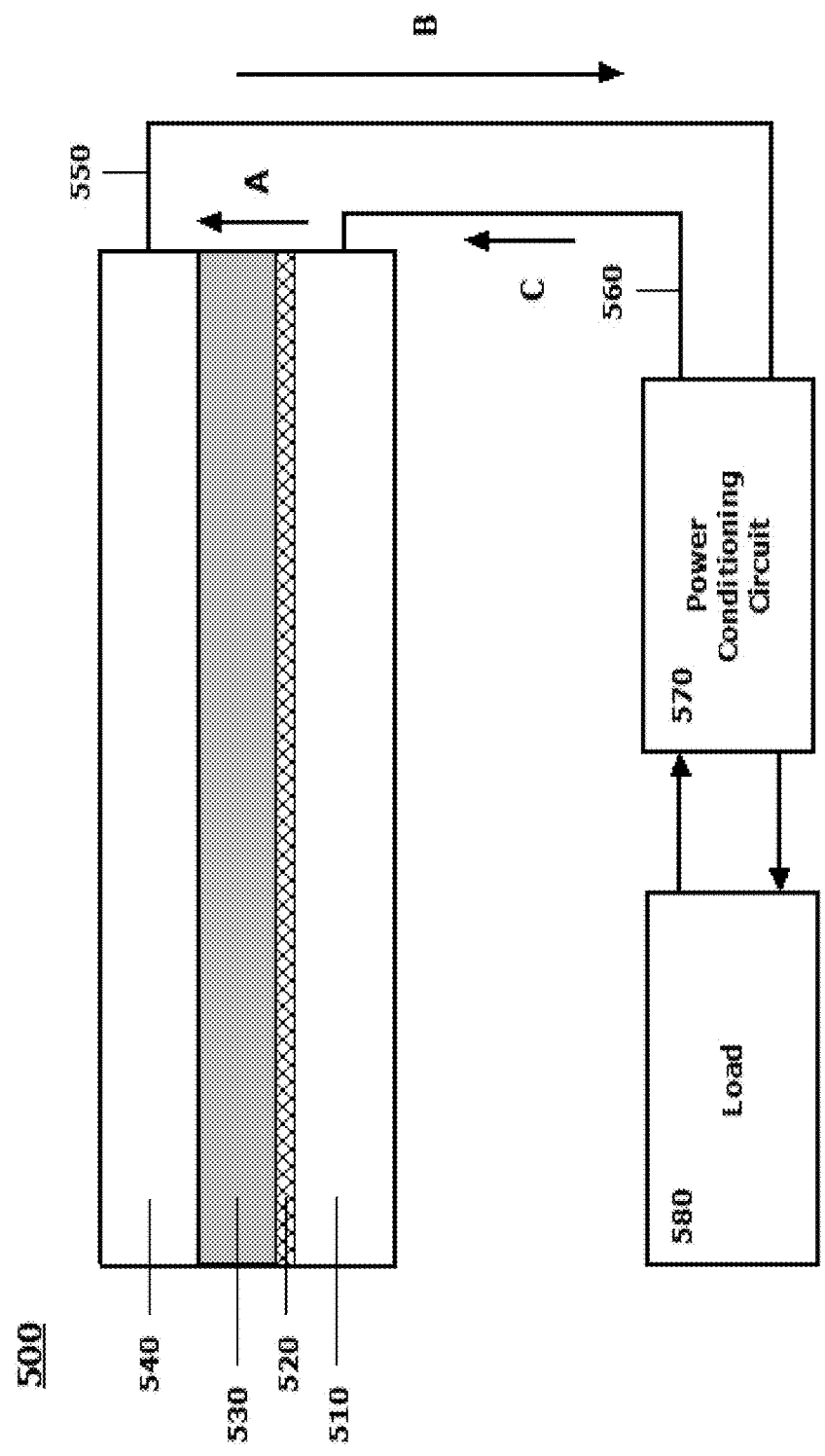
FIG. 5 illustrates a schematic diagram of an exemplary embodiment of an electrical circuit controlled device/load powered by an autonomous electrical power source component element according to this disclosure.

FIG. 5 illustrates a schematic diagram of an exemplary embodiment 500 of an electrical circuit controlled device/load powered by an autonomous electrical power source component element according to this disclosure. The arrangement of the autonomous electrical power source component element is in a form of the multi-layered component structure including at least a pair of opposing conductors 510, 540 set on either face of a thin dielectric layer 530. A low work function surface treatment, or low work function surface layer 520, may be applied to a surface of the conductor 510 to promote electron migration from the surface of the conductor 510, or from the surface layer 520 in a direction of a surface of an opposing conductor 540 in direction A as shown.

In order to obtain power from the autonomous electrical power source component element structure, leads 550, 560 may be connected for routing to and through a load 580 (which may include an electrically powered or controlled device). Controlling the current flow through the load 580 provides a capacity to power the load 580 at discrete intervals, or when properly modulated, substantially continuously. Load regulation may not be very good from the autonomous electrical power source component element itself. As such, the electrical power output may be conditioned by conditioning circuitry via, for example a power conditioning circuit 570. The power conditioning circuit 570 may perform a power regulation function. Appropriately conditioned, the available energy could provide a constant power source, or may be cycled. In embodiments, the load 580 may be matched to the power source and a continuous supply of power could be provided to an appropriately-sized load 580.

If a rate at which the electrons are returned through the external circuitry flowing from the conductor 540 of the autonomous electrical power source component element (the receptor surface conductor) through the lead 550 in direction B, optionally to a power conditioning circuit 570 and to and through the load 580, and then via the lead 560 in direction C to the conductor 510 (the donor surface conductor), the load 580 could be powered continuously and substantially forever. Conventional power conditioning or power matching concepts may be applicable to load match the load 580 to the available electrical power able to be continuously supplied from the autonomous electrical power source component element.

Figure 6:
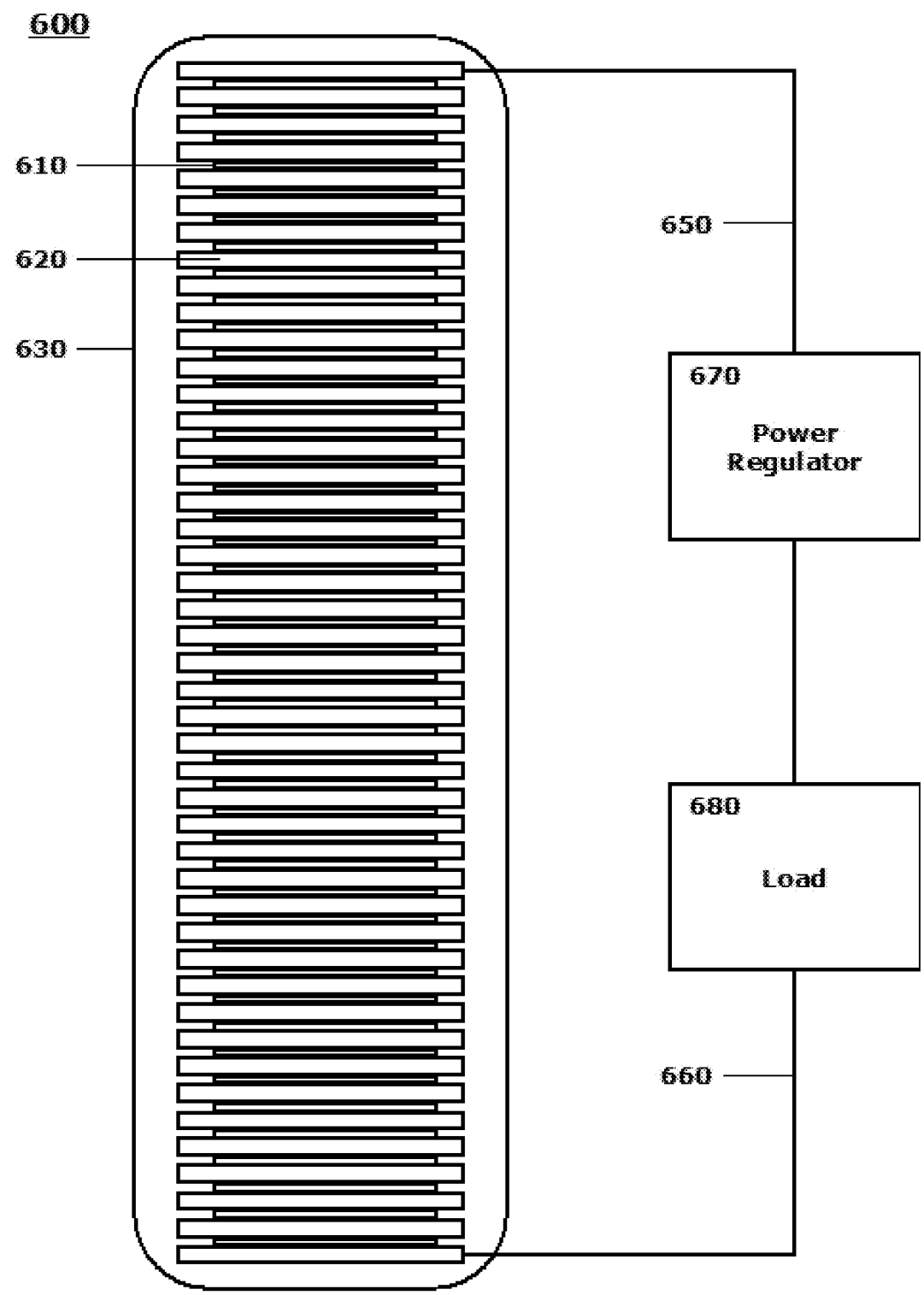
FIG. 6 illustrates a schematic diagram of an exemplary embodiment of an electrical circuit controlled device/load powered by an autonomous electrical power source component element, including a plurality of autonomous electrical power source component constituent elements electrically connected to each other, according to this disclosure.

FIG. 6 illustrates a schematic diagram of an exemplary embodiment 600 of an electrical circuit controlled device/load powered by an autonomous electrical power source component element including a plurality of autonomous electrical power source component constituent elements electrically connected to each other according to this disclosure. A structure of an autonomous electrical power source component element layers appropriately-sized numbers of autonomous electrical power source component constituent elements 610, configured as described above with reference to FIGS. 1-5, as stacks of upward to 100 constituent elements 610. Each of the autonomous electrical power source component constituent elements 610 may be on the order of tens of nanometers thick, and sandwiched between insulating layers 620, that may be on the order each of approximately 10 μm thick. The autonomous electrical power source component constituent elements 610 may be electrically connected in order to provide an autonomous electrical power source component structure that produces a usable electric power output.

Typically, the autonomous electrical power source component constituent elements 610 are generally thin and fragile. The hosting in the insulating layers 620 as a form of encasing structural components may enhance physical strength and usability, and provide a platform for connection, for example, of electrically interconnecting leads, and external wire leads 650, 660. An encasing structure or outer shell 630 may be generally comprised of an insulating material. This now-insulated stack of autonomous electrical power source component constituent elements 610 may then be further housed in, for example, a metallic structure or structure composed, or formed, of generally any other structurally-sound materials. Because the layers are thin themselves, transitional electrically-conducting contacts may be provided in contact with the layers to provide transition between the layers, and appropriately sized load-bearing wire leads 650, 660 for connecting the autonomous electrical power source component structure to a load 680 directly, or through some form of power regulator 670, for use. All of the elements depicted in FIG. 6 may then be housed as integral devices for accomplishing particular tasks. In embodiments, the load 680 may be in a form of (1) a sensor, the integral device performing a sensing operation; (2) a communication element, the integral device performing a communicating operation; (3) an alert/warning element, the integral device performing an alerting or warning function, providing one or more of a visual, audible or haptic indication of a condition of an environment in which the integral device is deployed and/or (4) an actuating element, the integral device performing an actuating function.

Voltage remains constant according to a fabrication or formation of the autonomous electrical power source component structure. Current scales with surface area of the opposing low work function and higher work function surfaces of each of the autonomous electrical power source component constituent elements, or an overall surface area of the opposing surfaces in the aggregate. As such, power scales roughly linearly with area (similar to a solar cell). More area causes migration of more electrons resulting, in turn, in more current at a same voltage when connected to a load.

As generally indicated above, a series (or stack) of sandwiched structures may be accumulated to a particular thickness of, for example, 50 to 100 (or more) individual autonomous electrical power source component constituent elements 610 between insulating layers 620, according to the dimensions indicated below, to increase the power out. Each of the individual autonomous electrical power source component constituent elements 610 may be considered an individual power source that is connectable in parallel or in series to others of the autonomous electrical power source component constituent elements 610, as appropriate.

As an example of a particular conducting layer, graphene has been experimentally explored as providing favorable physical and electrical conduction properties. An amount of thermal energy available at room temperature yields a theoretical maximum power density available in a range of approximately 1 W per gram. The disclosed schemes are directed to maximizing or optimizing a surface effect. In this regard, the surface area of the thin film structure that would equate to providing this 1 Watt would be on an order of 2630 $m^2$ of surface area, approximately 51 m×51 m.

For a particular surface area of the disclosed autonomous electrical power source component structure, a 10 $cm^2$ surface area (approximately 1.25×1.25 inches) for the accumulated or aggregated autonomous electrical power source component constituent elements 610 according to the disclosed schemes may produce approximately 190 nW. Those of skill in the art recognize that this is a small amount of power and may need to be increased for most applications. Ten square centimeters is a relatively large area when compared to microelectronic devices and products of low power consumption. To scale down the packaged area, and/or to scale up the power, multiple layers may be employed in the manner shown in FIG. 6. It should be noted that, because thermal energy from the environment must flow through the additional structural layers to the inner layers, some energy accumulation reduction will be experienced for each additional internal layer added. Thermal conduction losses through the layers and thermal impedance mismatches between layers may reduce the phonon flow from the environment by a factor of upwards to 5%.

An exemplary experimental autonomous electrical power source component structure approximately 10 $cm^2$ and 1 mm thick (comprising on the order of 50 internal layers, and an outer encasing layer of 12-15 mils (approximately 350 microns) is anticipated to be able to produce an electric potential of 1.2 V and an output power of 5 µW at room temperature. For reference, a typical electrically-powered men's wristwatch draws on an order of 1.0-1.2 µW.

In some "installations" or use cases, it will be appropriate to additionally encase the insulated autonomous electrical power source component constituent elements 610 of the component structure with the outer shell 630 that provides structural support and mounting for power leads 650, 660 exiting the autonomous electrical power source component structure. A typical outer shell 630 may comprise a layer on the order of 10 mils thick and may be comprised of, for example, polyether ether ketone (PEEK). A resultant thickness of a stacked configuration of an exemplary autonomous electrical power source component including 50 insulator-separated autonomous electrical power source component constituent elements 610 surrounded by an outer insulating shell 630 being in a range of 50 mils or less.

Figure 7:
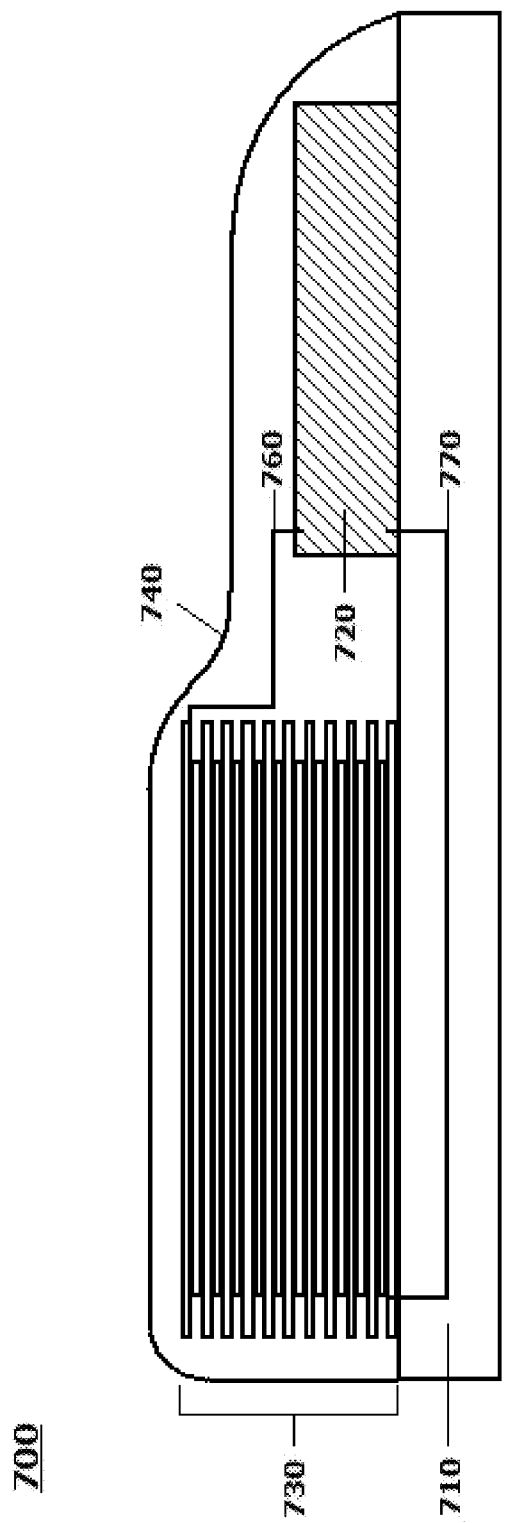
FIG. 7 illustrates a schematic diagram of an exemplary embodiment of an integrated package including at least one electrically-driven component powered by an autonomous electrical power source component element, including a plurality of autonomous electrical power source component constituent elements electrically connected to each other, according to this disclosure.

FIG. 7 illustrates a schematic diagram of an exemplary embodiment of an integrated package 700 including at least one electrically-driven component 720 powered by an autonomous electrical power source component 730, including a plurality of autonomous electrical power source component constituent elements electrically connected to each other, according to this disclosure.

As shown in FIG. 7, the integrated package 700 may include the at least one electrically-driven component 720 and the autonomous electrical power source component 730 being cooperatively mounted on a substrate 710, or otherwise mounted cooperatively with respect to one another. The autonomous electrical power source component 730 may be electrically connected to the at least one electrically-driven component 720 by power leads 760, 770. In embodiments, the at least one electrically-driven component 720 may be one or more of a sensor, communication, alert/warning, or actuating element. Cooperative placement of the autonomous electrical power source component 730 in a vicinity of any heat source may increase its efficiency, e.g., near a photo cell, or the at least one electrically-driven component 720, or a battery, or other mechanism that produces a thermal gradient. The at least one electrically-driven component 720 may not be 100% efficient, proximal placement of the autonomous electrical power source component 730 may allow generated excess heat to be "recycled" back into the autonomous power source component 730, thereby increasing overall efficiency. In embodiments, the autonomous electrical power source component 730 may be a back-up power source or an emergency power source for limited functionality under certain conditions, and not a primary power source.

Such an integrated package 700 may find broad application as the autonomous electrical power source component 730 may supply power to the at least one electrically-driven component 720 when the integrated package 700 is arranged to be embedded, for example, in a structural member. A capacity for the autonomous electrical power source component 730 to supply continuous or intermittent power to the at least one electrically-driven component 720 in a broad spectrum of installations allows the integrated package 700 to be emplaced in structures, environments and/or operating scenarios in which the integrated package 700 is not subjected to any external physical movement, distortion or the like, and in which routine access to the required source of power for the at least one electrically-powered components 720, for servicing, replacement, recharge, or replenishment, may be substantially impossible.

Incorporation of the autonomous electrical power source component 730 in a particular integrated package 700, particularly where an intention is to provide substantially continuous electrical power to the at least one electrically-driven component 720 may require proper scaling of the autonomous electrical power source component 730 to ensure the sustained capacity to provide necessary electrical power.

FIGS. 8A-8I illustrate schematic diagrams of a series of exemplary steps in a build process of an autonomous electrical power source component structure, including a plurality of autonomous electrical power source component constituent elements electrically connected to each other according to this disclosure.

Figure 8A:
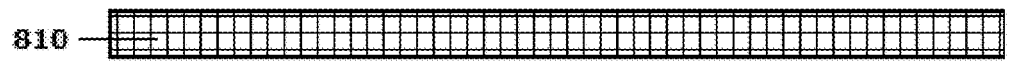
FIGS. 8A-8I illustrate schematic diagrams of a series of exemplary steps in a build process of an autonomous electrical power source component element, including a plurality of autonomous electrical power source component constituent elements electrically connected to each other, according to this disclosure.

As shown in FIG. 8A, an insulating layer 810 may be provided.

Figure 8B:
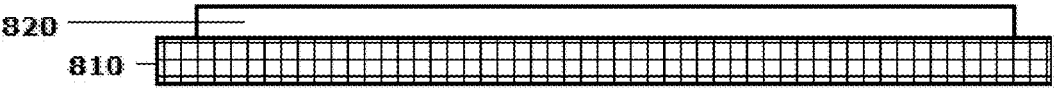

As shown in FIG. 8B, a conductor layer 820 may be provided on the insulating layer 810 according to the above-described configurations.

Figure 8C:
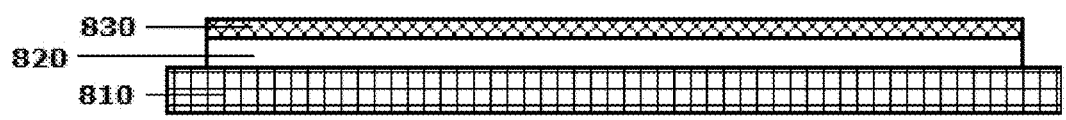

As shown in FIG. 8C, a surface of the conductor layer 820 may be conditioned, or may have adhered, or otherwise placed in close contact to it, a low work function layer 830, rendering the conductor layer 820 an electron donor or emitter layer, with the surface having a work function in a range of 1.0 eV or less.

Figure 8D:
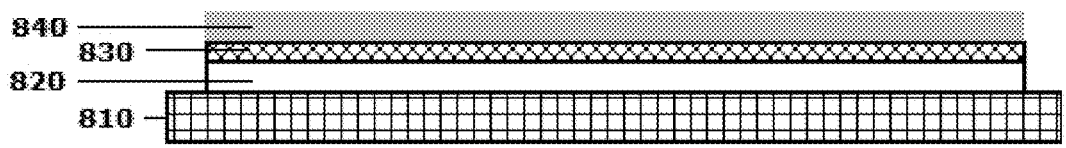

As shown in FIG. 8D, a dielectric layer 840 according to any one of the above-described embodiments, and having an overall finished thickness in a range of 200 nm or less, and preferably 100 nm or less, and in embodiments in a range of between 20 and 60 nm, may be deposited on the low work function layer 830.

Figure 8E:
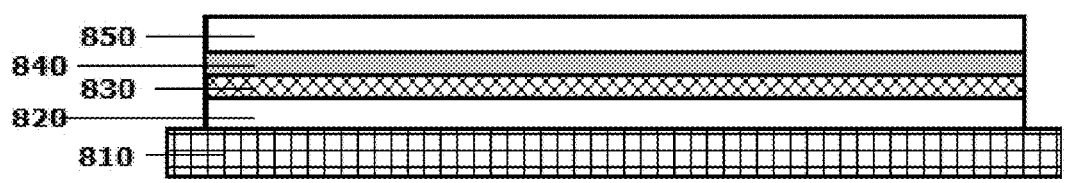

As shown in FIG. 8E, another conductor 850 may be brought into contact with the dielectric layer 840. The conductor 850 may have a comparatively higher work function (2.0 eV or more) facing surface layer. The positioning of the conductor 850 on the dielectric layer 840 may complete the formation of a first autonomous electrical power source component constituent element.

Figure 8F:
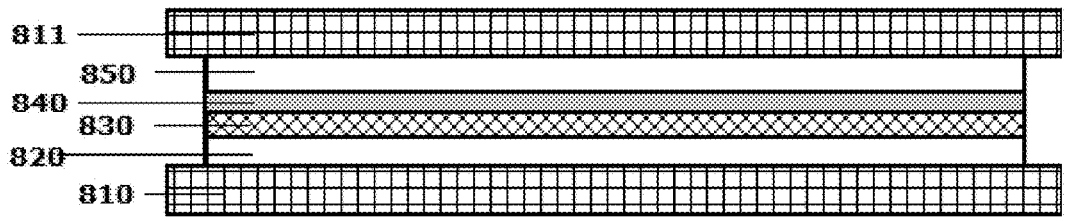

As shown in FIG. 8F, the build process may continue by providing another insulator layer 811 in contact with the conductor 850 thereby encasing the first autonomous electrical power source component constituent element between two insulator layers 810, 811.

Figure 8G:
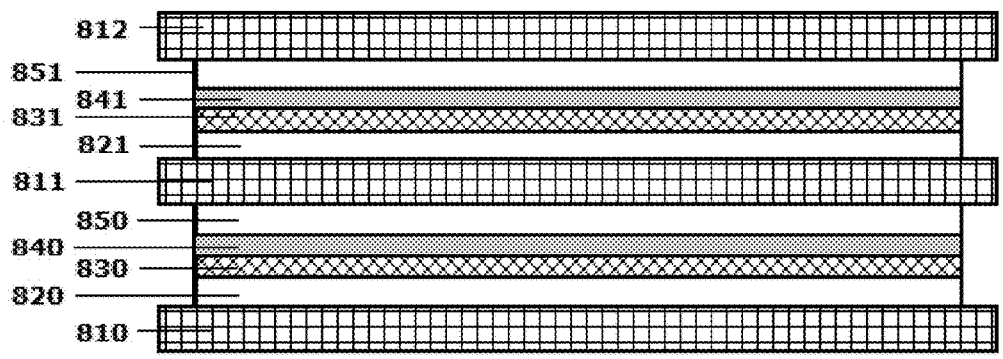

As shown in FIG. 8G, the build process depicted in FIGS. 8A-8 F may be repeated in a manner that provides additional autonomous electrical power source component constituent elements between insulator layers to construct an autonomous electrical power source component as shown, for example, in FIG. 6, with the addition of a conductor layer 821, a low work function layer 831, a dielectric layer 841, a conductor layer 851, and another insulator layer 812.

Figure 8H:
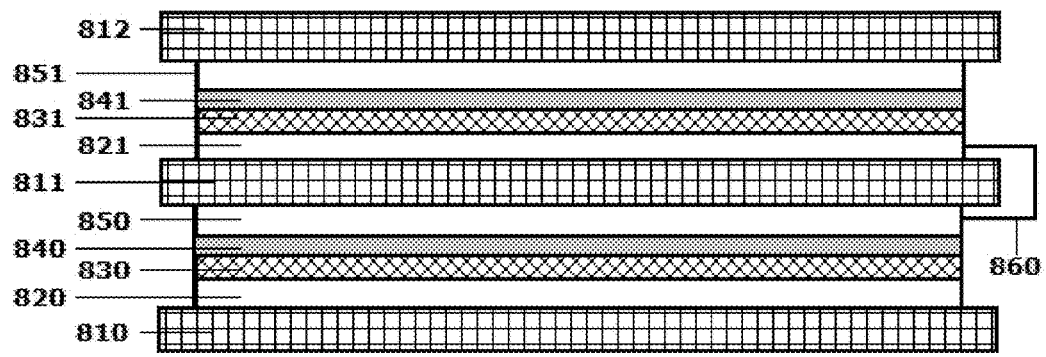

As shown in FIG. 8H, the respective autonomous electrical power source component constituent elements may be connected in series using an internal conductor 860.

Figure 8I:
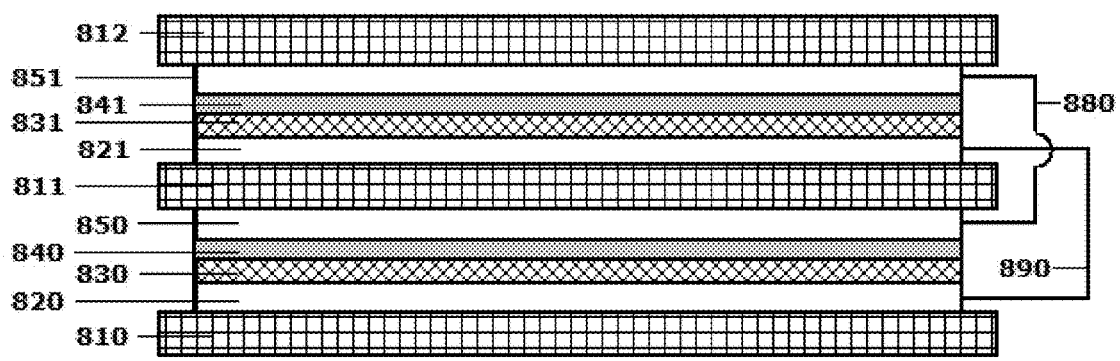

As shown in FIG. 8I, the respective autonomous electrical power source component constituent elements may be connected in parallel using internal conductors 880 and 890.

It should be noted that the above process may be repeated a number of times until an appropriate number of layers constituting an autonomous electrical power source component is completed. An objective of the build process may be to increase the overall surface area of the opposing conductors in the aggregate.

Figure 9:
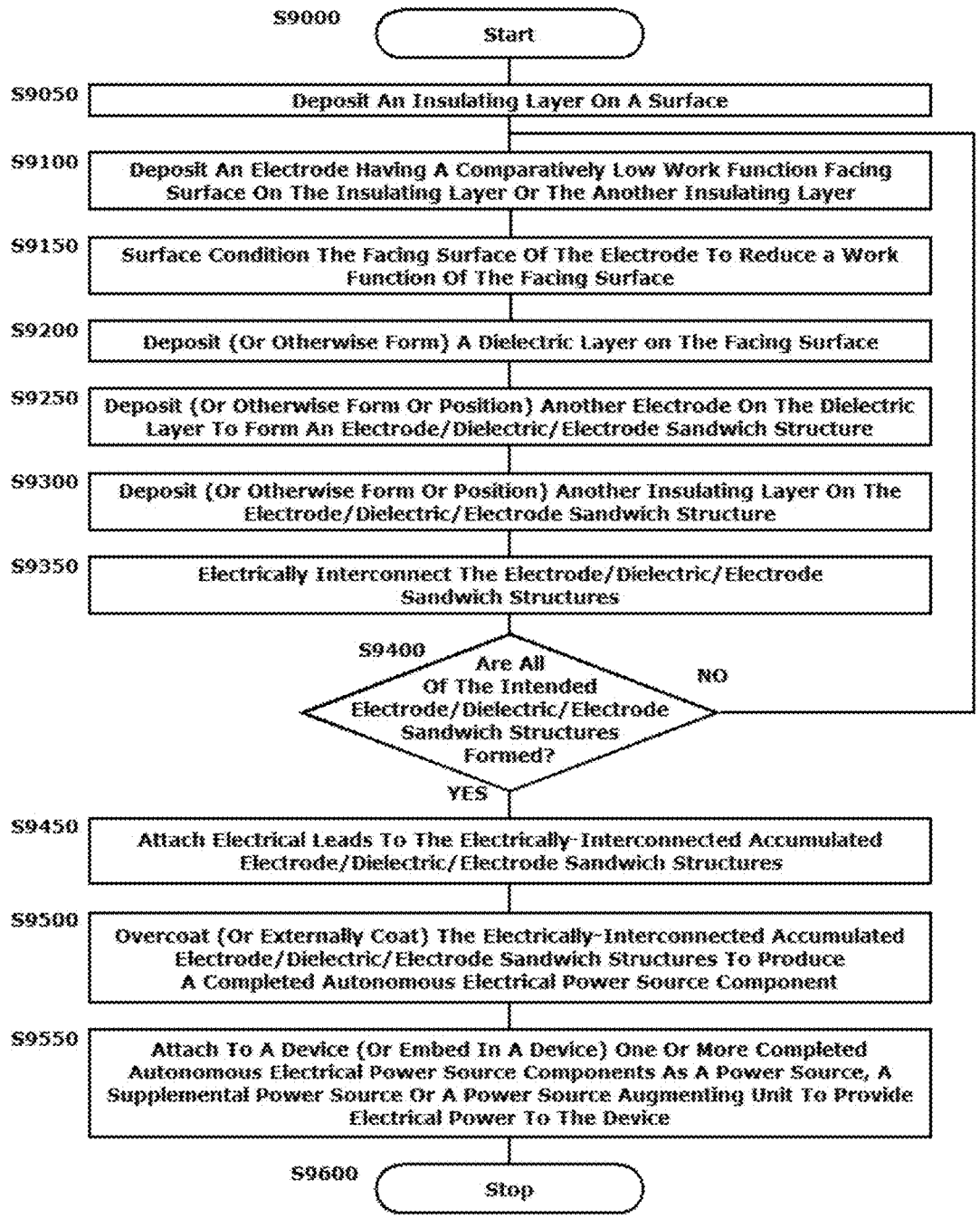
FIG. 9 illustrates a flowchart of an exemplary method for executing a build process for an autonomous electrical power source component element, including a plurality of autonomous electrical power source component constituent elements electrically connected to each other, according to this disclosure.

The disclosed embodiments may include a method for executing a build process for an autonomous electrical power source component including a plurality of autonomous electrical power source component constituent elements electrically connected to each other. FIG. 9 illustrates a flowchart of such an exemplary method. As shown in FIG. 9, operation of the method commences at Step S9000 and proceeds to Step S9050.

In Step S9050, an insulating layer may be deposited or formed on a surface according to any known material deposition method. In embodiments, the insulating layer may be presented as a solid structural component placed on the surface. In embodiments, an insulating layer component may be on an order of 10 µm thick for a stand-alone autonomous electrical power source component, or if deposited, for example, on a structural elemental surface, which may include a structure for supporting additional elements, including at least one electrically-powered device or element, to produce an integrated device, may be on an order of 1 µm thick. Operation of the method proceeds to Step S9100.

In Step S9100, an electrode, which may be configured to have a comparatively low work function (on an order of 1.0 eV or less) outward or upward facing surface, may be deposited on the insulating layer. In embodiments, an electrode material may be deposited or placed on the insulating layer and additional measures may be taken to render the facing surface of the electrode formed of the electrode material to have a low work function (in a range of 1.0 eV or less). In embodiments, the electrode material may be graphene and the graphene layer may be only multiple Ångströms thick. Operation of the method proceeds to Step S9150.

In Step S9150, the facing surface of the electrode material may be surface conditioned to reduce a work function of the facing surface to 1.0 eV or less, according to any of the mechanisms described above. In embodiments, the low work function surface of the electrode may be integral to the electrode, or may be an additional layer in intimate contact with the facing surface of the electrode. Operation of the method proceeds to Step S9200.

In Step S9200, a dielectric layer may be deposited or otherwise formed on the conditioned low work function facing surface of the conductor, or on the low work function layer in intimate contact with the facing surface of the conductor. The dielectric layer may be in a range of less than 200 nm thick, and preferably in a range of less than 100 nm thick. In embodiments, the dielectric layer may be in a range of between 20 nm and 60 nm thick. In embodiments, the dielectric layer may be formed as a substantially homogeneous single material structure. In separate embodiments, the dielectric layer may be formed of multiple materials, including multiple materials in multiple layers. In embodiments, the dielectric layer may be formed in a manner that produces a non-linear profile when viewed from at least one edge of the dielectric layer. In embodiments, at least a portion of the dielectric layer may be formed to have conically- or pyramidal-shaped structures with a thin end being in contact with the low work surface layer and a thick end facing away from the low work surface layer in a direction orthogonal to the low work surface layer. Operation of the method proceeds to Step S9250.

In Step S9250, another electrode may be deposited, or otherwise formed or positioned, on the dielectric layer to form an electrode/dielectric/electrode sandwiched structure referred to throughout this disclosure as an autonomous electrical power source component constituent element. The another electrode may have a facing surface layer that faces the dielectric on which the another electrode is formed, the facing surface layer of the another electrode having a work function substantially higher (2.0 eV or greater) than the work function of the facing surface of the first-placed electrode, or the work function of the low work function layer placed in intimate contact with the first-placed electrode. In embodiments, the another electrode may be formed of a deposited metal composition or material. Operation of the method proceeds to Step S9300.

In Step S9300, another insulating layer may be deposited, or otherwise formed or positioned, on the electrode/dielectric/electrode sandwiched structure comprising the first autonomous electrical power source component constituent element. The combination of insulating layers may provide physical protection for the autonomous electrical power source component constituent elements, electrical isolation from other autonomous electrical power source component constituent elements in a stacked configuration of an autonomous electrical power source component, and a more substantial material structure through which electrode connections may be made to the autonomous electrical power source component. Operation of the method proceeds to Step S9350.

In Step S9350, the electrodes of the electrode/dielectric/electrode autonomous electrical power source component constituent elements may be electrically interconnected with electrodes of other autonomous electrical power source component constituent elements when being formed as a multiple autonomous electrical power source component constituent element stacked autonomous electrical power source component structure. Operation of the method proceeds to Step S9400.

Step S9400 is a determination step in which it is determined whether all of the intended electrode/dielectric/electrode sandwiched structures comprising each of the autonomous electrical power source component constituent elements are formed in a manner to comprise the overall intended composition of the autonomous electrical power source component structure. In embodiments, there may be at least 50 separate insulator-separated autonomous electrical power source component constituent elements electrically interconnected to one another. In embodiments, there may be as many as 100 or more separate insulator-separated autonomous electrical power source component constituent elements electrically interconnected to one another. At present, a practical upper limit to a number of insulator separated autonomous electrical power source component constituent elements according to the disclosed embodiments has not been established. In this regard, a number of separate insulator-separated autonomous electrical power source component constituent elements electrically interconnected to one another may exceed 100.

If in Step S9400, it is determined that all of the intended insulator-separated autonomous electrical power source component constituent elements have not been formed in a manner that completes the intended stack, operation of the method reverts to Step S9100.

If in Step S9400, it is determined that all of the intended insulator-separated autonomous electrical power source component constituent elements have been formed in a manner that completes the intended stack, operation of the method proceeds to Step S9450.

In Step S9450, electrical leads may be attached to the electrically-interconnected accumulated electrode/dielectric/electrode sandwich structures as the autonomous electrical power source component constituent elements comprising the stacked autonomous electrical power source component structure. Operation of the method proceeds to Step S9500.

In Step S9500, the electrically-interconnected accumulated electrode/dielectric/electrode sandwiched structures each comprising an individual autonomous electrical power source component constituent element, which in combination compose an overall stacked autonomous electrical power source component structure, may be over coated or otherwise externally coated with an encasing material, or an encasing structure, to produce a completed autonomous electrical power source component. Operation of the method proceeds to Step S9550.

In Step S9550, one or more completed autonomous electrical power source component structures may be attached to, or embedded in, a device as a power source, a supplemental power source, or a power source augmenting unit to provide electrical power to the device. Operation of the method proceeds to Step S9600, where operation of the method ceases.

As is described in some detail above, the systems and methods according to this disclosure may be directed at providing autonomous, or supplemental, power to electronic systems, electronic devices, and/or electrically-powered system components, including communication, sensor, and actuating elements.

Figure 10:
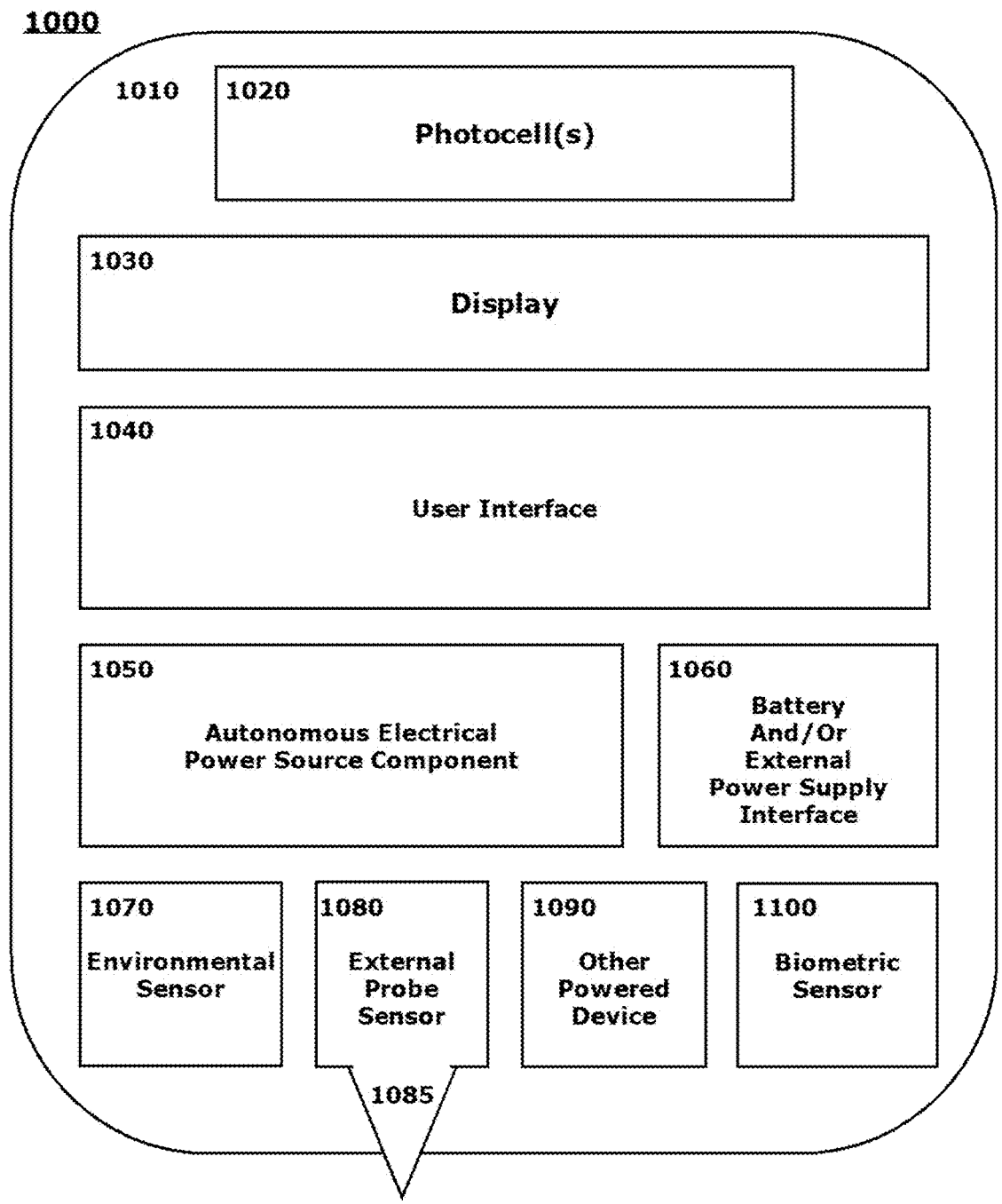
FIG. 10 illustrates a schematic diagram of an exemplary device incorporating at least one autonomous electrical power source component according to this disclosure as a power source, or as a supplement to a battery, a photocell or another power source for powering the exemplary device.

FIG. 10 illustrates a schematic diagram of an exemplary device 1000 incorporating at least one autonomous electrical power source component according to this disclosure as a power source, or as a supplement to a battery, a photocell or another power source for powering the exemplary device. As shown in FIG. 10, the exemplary device 1000 may have a body structure 1010 for housing multiple elements. Not all of the elements shown in exemplary manner in FIG. 10 may necessarily be present in any individual embodiment of a particular powered device.

One or more photocells 1020 may be provided in a face of the exemplary device 1000 to provide power to components within the exemplary device 1000. In this regard, photocells are only an example of a supplemental energy harvesting technology usable in the exemplary device 1000. For example, triboelectric devices are under wide-spread development as are RF harvesters and other methods of harvesting various sources of ambient energy, any of which could be included additionally, or as a substitute for the photocells 1020 in the exemplary device. Separately, or additionally, the exemplary device may be powered by a battery or other external power supply (or power supply interface) 1060. One or more autonomous electrical power source components or units 1050 may be provided in the exemplary device 1000 as a stand-alone power source, a power source for individual components within the exemplary device, or as a supplemental power source to provide bridging or sustaining power when any power recoverable from the photocells 1020 or the battery and/or external power supply (or interface) 1060 becomes interrupted, or otherwise unavailable.

The exemplary device 1000 may include a display component 1030 which may be independently powered by any one of the available power sources, including being autonomously powered by one or more of the autonomous electrical power source components or units 1050.

The exemplary device 1000 may include a user interface 1040 which may be of any known composition by which a user may interact with the exemplary device 1000.

The exemplary device 1000 may include an environmental sensor 1070. The environmental sensor 1070 may be in a form of, for example, a temperature sensor, a humidity sensor, a CO sensor, a smoke detector, a radon detector, a radiation detector, a hazardous material/substance detector, or other similar sensor, detector or sensing or detecting element for sensing one or more environmental parameters.

The exemplary device 1000 may include an external probe-type sensor 1080 by which a user may use the external probe 1085 to sense any one of a number of parameters associated with an environment surrounding the exemplary device 1000 and/or a material, structure or body with which the external probe sensor may be brought into proximity, near contact, or actual contact. Such an external probe-type sensor 1080 may, for example, sense macro-vibrations of the material, structure or body, or of the device itself, seismic activity, or sensed motion in a vicinity of the device. The external probe 1085 may be in a form of a physical, proximity, optical or other known probe element. In this context, the macro vibrations have to do with the movement of a device or body structure, rather than the micro-vibrational energy produced at the electron level on which the energy harvesting capacity of the disclosed schemes is based.

The exemplary device 1000 may include some manner of biometric sensor 1100 by which a particular biometric parameter of a human body, an animal body, or another living body or organism structure, may be evaluated. For human body parameter detection, the biometric sensor 1100 may provide the exemplary device 1000 with a capacity, for example, to make a therapeutic diagnosis of a condition of the human body, or to monitor particular parameters by which to aid in medical diagnosis of a condition of the human body.

The exemplary device 1000 may include any other powered device 1090, including actuators, data processing elements, and/or wireless communicating components, that may be electrically-powered by any one of the available power sources including particularly by one or more autonomous electrical power source components or units.

The unique capacity of the disclosed embodiments of the autonomous electrical power source components or units to operate when embedded in structures provides a capacity to internally assess parameters of the structures in which detection elements may be embedded. Stress, deterioration, structural breakdown and the like are all subject to routine monitoring and reporting.

The above-described exemplary systems and methods reference certain conventional components, sensors, materials, and real-world use cases to provide a brief, general description of suitable operating, energy harvesting, and electrical power production environments in which the subject matter of this disclosure may be implemented for familiarity and ease of understanding.

Those skilled in the art will appreciate that other embodiments of the disclosed subject matter may be practiced in many disparate electronic systems, electronic/electrical devices, or electrically-powered system components of many different configurations.

The exemplary depicted sequence of executable instructions represent one example of a corresponding sequence of acts for implementing the functions described in the steps of the above-outlined exemplary method. The exemplary depicted steps may be executed in any reasonable order to carry into effect the objectives of the disclosed embodiments. No particular order to the disclosed steps of the methods is necessarily implied by the depiction in FIG. 9 except where a particular method step is a necessary precondition to execution of any other method step.

The disclosed schemes may provide, for example, a coin cell size device that produces the same output as a coin cell battery in virtually any structure or environment. As such, the yield is comparable to current small battery technology for driving small electronic devices in a package that is comparatively environmentally friendly and producible at a same or a less cost than the small battery. Further, the disclosed structures are generally perpetual in their capacity to produce usable electrical output in virtually any employment scenario, including those in which no external physical stimulation is available to the autonomous electrical power source components or units. The disclosed schemes may provide an autonomous electrical power source component that is capable of operating at a temperature above absolute zero and in an ambient light devoid environment, which may also be devoid of RF, mechanical and other forms of ambient energy.

The disclosed schemes may include autonomous electrical power source component structures that may include one or more layers being laminated together in a conventional laminating process to produce the stacked layer components described above.

The disclosed schemes may provide a unique energy harvesting capability from minimal thermal energy that was unforeseen as it realistically may have been viewed by those of skill in the art as presenting a concept that, on its face, appears to be in contravention of the Second Law of Thermodynamics, which is an empirical law that is not provable. The Second Law of Thermodynamics teaches that at least two heat sources be provided with one at a lower potential than the other. Based on the heat flow of one to the other, the differential is converted to energy. This is what gives rise to the operation of a steam engine, a thermoelectric generator (TEG), the thermocouple and the like. More specifically stated, there is an energy release based on a flow of energy from a heat source to a heat sink. So in essence, the Second Law says that given a temperature differential there is an energy generation. The difficulty is that when reduced to equations, the equations based on the Second Law of Thermodynamics are reduced to zero for equal temperature (equal potential) surfaces. In other words, the Second Law of Thermodynamics would seem to imply that there is no energy recovery available from two sources at substantially a same temperature in a sealed system. One of skill in the art, given the Second Law of Thermodynamics, would likely conclude that no charge difference is possible. It has, however, been mathematically proven that certain electron migration may occur given certain constraints (according to standard physics techniques). As such, it has been proven, that one can get work out of a single thermal reservoir of uniform temperature simply due to the molecular motion inherent in all formed bodies.

Extensive experimentation resulted in the disclosed schemes that present a very thin collector layer, and a very thin emitter layer, each of which may be of a thickness on the order of an atomic layer, i.e. 3 Å or 0.33 nm, and bring them into very close, non-contact proximity (less than 200 nm), typically on either side of the intervening layer of a comparable thickness formed of a dielectric material. The disclosed schemes implement a type of thermal energy harvesting because, at absolute zero, there is no energy harvesting capability. Thermal energy, in the context of this disclosure, and as is generally understood, is the amount of energy in a particular substance due to its molecular vibration or motion. If a substance is heated, even a little above absolute zero, everything in the substance is moving around a little faster and it has a certain internal energy.

Although the above description may contain specific details, they should not be construed as limiting the claims in any way. Other configurations of the described embodiments of the disclosed systems and methods are part of the scope of this disclosure.

It will be appreciated that various of the above-disclosed and other features and functions, or alternatives thereof, may be desirably combined into many other different systems or applications. Also, various alternatives, modifications, variations or improvements therein may be subsequently made by those skilled in the art which are also intended to be encompassed by the following claims.

We claim:

1. A method for forming an embeddable integrated electrical package, comprising:
   providing at least one electrically-driven component;
   forming an electrical power source component configured to provide an electrical energy source for the at least one electrically-driven component by
      arranging a first conductor, formed of a first conductive material and having a first surface and a second surface, on a build surface with the first surface of the first conductor facing away from the build surface,
      conditioning the first surface of the first conductor to have a work function in a range of 1.0 electron volts (eV) or less,
      forming a dielectric layer with a thickness of 200 nm or less over the conditioned first surface of the first conductor, and
      arranging a second conductor, formed of a second conductive material and having a first surface with a work function in a range of 2.0 eV or greater, and a second surface, over the formed dielectric layer such that the first surface of the second conductor faces the dielectric layer,
   the first conductor, the dielectric layer and the second conductor forming a layered structure of an electrical power source component element;
   connecting a first electrical lead and a second electrical lead between the at least one electrically-driven component and the electrical power source component to electrically connect the electrically driven component and the electrical power source component; and
   encasing the at least one electrically-driven component and the electrical power source component in a common outer shell to provide the embeddable integrated electrical package.

2. The method of claim 1, a structure of the electrical power source component having a thickness in a range of less than 5 mils.

3. The method of claim 1, the conditioning of the first surface of the first conductor comprising surface treating the first surface of the first conductor to lower the work function of the first surface to be in the range of 1.0 eV or less.

4. The method of claim 1, the conditioning of the first surface of the first conductor comprising arranging a separate material layer having a work function in the range of 1.0 eV or less on the first surface of the first conductor.

5. The method of claim 4, the separate material layer being formed to have a thickness in a range of 1 nm or less.

6. The method of claim 1, the first conductor and the second conductor each having a thickness in a range of 10 nm or less.

7. The method of claim 1, the conductive material from which the first conductor is formed being graphene.

8. The method of claim 1, the dielectric layer having a thickness in a range of 100 nm or less and being sandwiched between the first surface of the first conductor and the first surface of the second conductor.

9. The method of claim 8, the dielectric layer having a thickness in a range of 20 nm to 60 nm.

10. The method of claim 8, the dielectric layer varying in thickness across a planform of the dielectric layer between the first surface of the first conductor and first surface of the second conductor.

11. The method of claim 1, the dielectric layer being formed at least in part of a plurality of tapered shapes, each of the plurality of tapered shapes having a tapered structure in which a cross-sectional area of the each of the plurality of tapered shapes is comparatively larger at an end facing the first surface of the second conductor and comparatively smaller at an end facing the first surface of the first conductor.

12. The method of claim 1, the dielectric layer being a porous layer, pores in the porous layer being filled at least in part with a metal cation.

13. The method of claim 1, the electrical power source component being comprised of a plurality of electrical power source component elements and a plurality of insulating layers arranged in a stacked structure,
   the plurality of electrical power source component elements being separated by the plurality of insulating layers in the stacked structure, and
   the plurality of electrical power source component elements being electrically interconnected with one another.

14. The method of claim 13, each of the plurality of insulating layers having a thickness of less than 10 μm.

15. The method of claim 13, the electrical power source component further comprising an outer insulating layer substantially encasing the stacked structure.

16. The method of claim 13, the first electrical lead being electrically connected to an uppermost electrical power source component element in the stacked structure and the second electrical lead being electrically connected to a lowermost electrical power source component element in the stacked structure.

17. The method of claim 1, further comprising embedding the embeddable integrated electrical package as an integral portion of a structural member.

18. The method of claim 17, the structural member substantially fully encasing the embeddable integrated electrical package.

19. The method of claim 17, the structural member being one of a portion of a building structure or a portion of a vehicle structure.

20. The method of claim 1, the at least one electrically-driven component comprising one or more of an environmental sensor, a seismic sensor, a wireless communicating component, and a haptic alert/warning device.

* * * * *